US00PP08107P

United States Patent [19]

van der Knapp

[11] Patent Number: Plant 8,107

[45] Date of Patent: Jan. 19, 1993

[54] CHRYSANTHEMUM PLANT—GIRAFFE CULTIVAR

[75] Inventor: Jacques C. M. van der Knapp, De Lier, Netherlands

[73] Assignee: Fides Beheer B.V., De Lier, Netherlands

[21] Appl. No.: 720,584

[22] Filed: Jun. 25, 1991

[51] Int. Cl.[5] ..... A01H 5/00

[52] U.S. Cl. ..... Plt./82.1

[58] Field of Search ..... Plt./74, 82.1

[56] References Cited

U.S. PATENT DOCUMENTS

| | | | |
|---|---|---|---|
| P.P. 5,870 | 2/1987 | van der Jagt | Plt. 74 |
| P.P. 5,984 | 5/1987 | Duffett | Plt. 74 |
| P.P. 6,744 | 4/1989 | van der Knaap | Plt. 74 |
| P.P. 6,881 | 6/1989 | VandenBerg | Plt. 74 |
| P.P. 7,019 | 9/1989 | VandenBerg | Plt. 74 |

*Primary Examiner*—Howard J. Locker

*Attorney, Agent, or Firm*—Burns, Doane, Swecker & Mathis

[57] ABSTRACT

A new and distinct cultivar of Chrysanthemum plant named Giraffe is provided. The new cultivar was the result of a controlled breeding program wherein the Buffalo cultivar (non-patented in the United States) was pollinated by an unnamed seedling formed by crossing the Delta cultivar (U.S. Plant Pat. No. 5,815) by the BZN cultivar (non-patented in the United States). More specifically, the new cultivar forms attractive relatively large clear white single flowers having a yellow-green center (as illustrated). The inflorescence commonly exhibits two or three rows of petals. The response period of the flowers is approximately eight and one-half weeks. Resistance to white rust is exhibited. The new cultivar is particularly suited for use in the production of a cut single spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Giraffe.

The new cultivar is the product of a planned breeding program which had as its objective the creation of a new Chrysanthemum cultivar which exhibits attractive relatively large single white flowers, resistance to white rust, dark green foliage, and the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1985 at De Lier, The Netherlands. The female parent (i.e., the seed parent) was the Buffalo cultivar (non-patented in the United States) and the male parent (i.e., the pollen parent) was an unnamed seedling formed by crossing the DELTA cultivar (U.S. Plant Pat. No. 5,815) by the BZN cultivar (non-patented in the United States). The parentage of the new cultivar can be summarized as follows:

Buffalo × (Delta × BZN).

The seeds resulting from the above pollination were sown and plantlets were obtained which were physically and biologically different from each other. Selective study during September, 1986 resulted in the identification of a single plant of the new variety.

It was found that the new cultivar of the present invention:

(a) exhibits attractive relatively large clear white single flowers commonly comprising two or three rows of petals which have a yellow-green center,
(b) bears flowers in a generally flat capitulum configuration when mature,
(c) exhibits a flower response period of approximately eight and one-half weeks,
(d) exhibits resistance to white rust,
(e) forms attractive dark green foliage, and
(f) has the ability to produce flowers of commercially acceptable quality throughout the year in a cut mum production program.

Asexual reproduction of the new cultivar by cuttings initially taken during November, 1986, as performed at De Lier, The Netherlands, in a controlled environment has demonstrated that the characteristics of the new cultivar as herein disclosed are firmly fixed and are retained through successive generations of asexual propagation.

Giraffe has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Rhino cultivar (U.S. Plant Pat. No. 6,744), the Giraffe cultivar is found to form slightly less vegetative growth (e.g., assumes a height of approximately 90 cm. vs. approximately 100 cm.), exhibits a faster response period (e.g. approximately 8.5 weeks vs. approximately 9 weeks), forms smaller darker leaves, and exhibits resistance to white rust unlike the Rhino cultivar. The flower type, ray floret color, and the tolerance to low temperature of the Giraffe cultivar are substantially identical to the corresponding characteristics of the Rhino cultivar. The response periods identified herein are those typically exhibited in The Netherlands under optimum growing conditions. Under less advantageous growing conditions the response time may be slightly extended.

BRIEF DESCRIPTION OF THE PHOTOGRAPH

The accompanying photograph shows as nearly true as it is reasonably possible to make the same in a color illustration of this character, a typical specimen of an overal plant of the new cultivar. The plant was grown in a greenhouse at De Lier, The Netherlands.

DETAILED DESCRIPTION

The chart used in the identification of colors descrobed hereafter is the R.H.S. Colour Chart of the Royal Horticultural Society, London, England. The color values were determined at 11:00 a.m. to 12:00 noon under natural daylight conditions at De Lier, The Netherlands, on Mar. 13, 1991. The plants described were grown under standard green house conditions which approximate those commonly utilized for the production of cut mums.

Classification:

*Botanical.*—*Chrysanthemum morifolium* Ramat., cv. Giraffe.

*Commercial.*—Cut single spray.

INFLORESCENCE

A. Capitulum:

*Form.*—Generally flat when mature.

*Type.*—Single.

*Diameter across face.*—Approximately 75 to 85 mm. on average.

B. Corolla of ray and disc florets:

*Color (General tonality from a distance of three meters).*—*White with yellow-green center when mature.*

*Color ray florets.*—Top surface — Clear White, White Group 155D. Under surface — Clear White, White Group 155D.

*Color disc florets.*—Yellow-Green Group 144A when immature, and Yellow-Green Group 144C to yellow when mature.

C. Reproductive organs:

*Androecium.*—Present in disc florets.

*Gynoecium.*—Present in disc florets.

PLANT

A. General appearance:

*Height.*—Approximately 90 cm. on average.

B. Foliage:

*Color(upper surface).*—Yellow-Green Group 147A.

*Color (under surface).*—Yellow-Green Group 147B.

I claim:

1. A new and distinct cultivar of Chrysanthemum plant names Giraffe, substantially as herein shown and described, which:

(a) exhibits attractive relatively large clear white single flowers commonly comprising two or three rows of petals which have a yellow-green center, (b) bears flowers in a generally flat capitulum configuration when mature, (c) exhibits a flower response period of approximatel eight and one-half weeks, (d) exhibits resistance to white rust, (e) forms attractive dark green foliage, and )f) has the ability to produce flowers of commercially acceptable quality throughout the year in a cut mum production program.

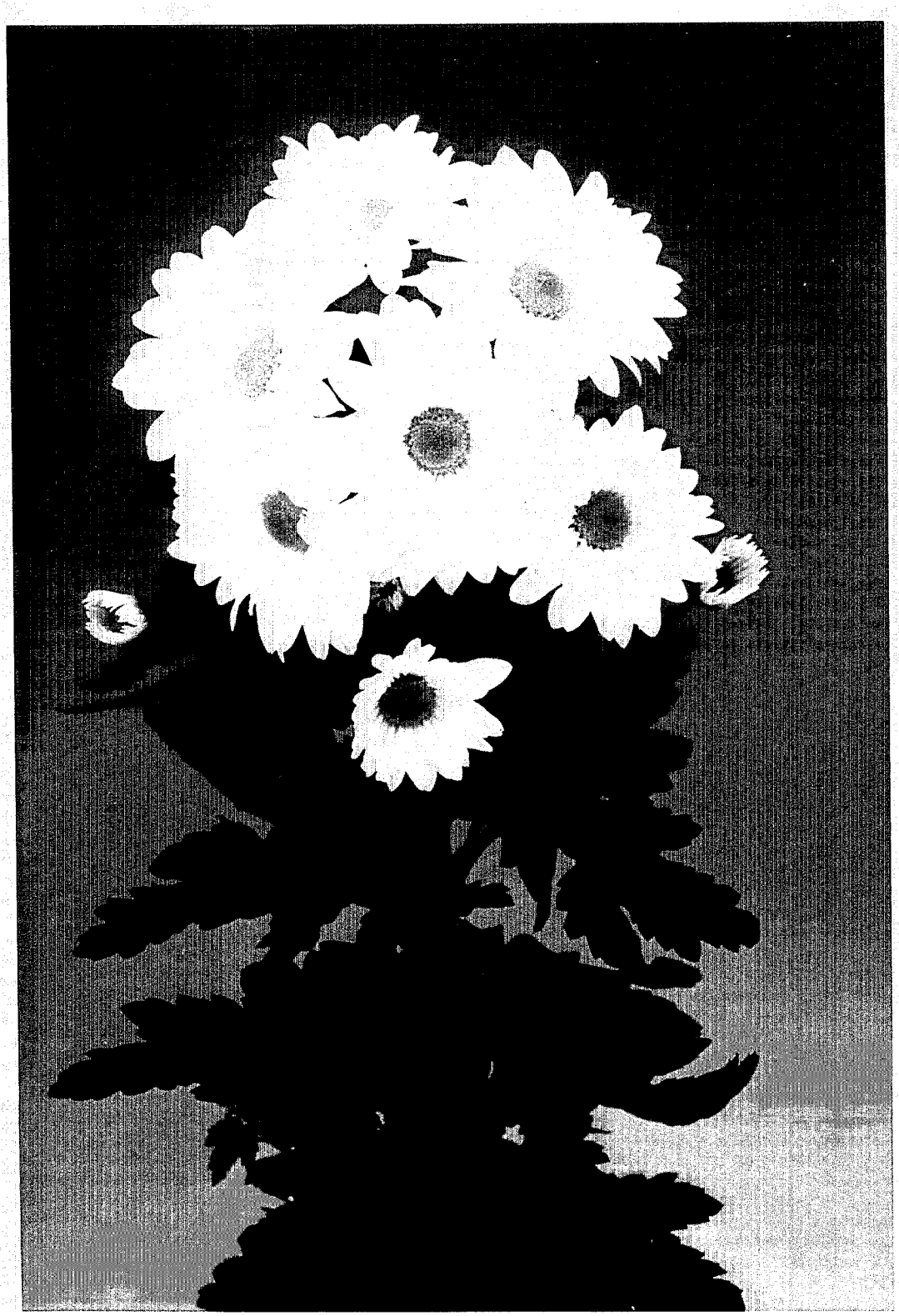

* * * * *